United States Patent
Leavitt et al.

(10) Patent No.: US 10,734,100 B2
(45) Date of Patent: Aug. 4, 2020

(54) SYSTEMS AND METHODS FOR TISSUE SAMPLE PROCESSING

(71) Applicant: Leavitt Medical, Inc., Orem, UT (US)

(72) Inventors: Matthew O. Leavitt, Salt Lake City, UT (US); Sorin Musat, Bucharest (RO)

(73) Assignee: Leavitt Medical, Inc., Lehi, UT (US)

( * ) Notice: Subject to any disclaimer, the term of this patent is extended or adjusted under 35 U.S.C. 154(b) by 283 days.

(21) Appl. No.: 15/893,061

(22) Filed: Feb. 9, 2018

(65) Prior Publication Data
US 2018/0226138 A1     Aug. 9, 2018

Related U.S. Application Data

(60) Provisional application No. 62/556,910, filed on Sep. 11, 2017, provisional application No. 62/457,078, filed on Feb. 9, 2017.

(51) Int. Cl.

| | | |
|---|---|---|
| *G16H 10/40* | (2018.01) | |
| *B01L 3/00* | (2006.01) | |
| *G01N 1/31* | (2006.01) | |
| *G16H 80/00* | (2018.01) | |
| *G16H 30/40* | (2018.01) | |
| *G16H 10/60* | (2018.01) | |
| *G01N 35/00* | (2006.01) | |
| *G16H 50/20* | (2018.01) | |

(52) U.S. Cl.
CPC .............. *G16H 10/40* (2018.01); *B01L 3/508* (2013.01); *G01N 1/312* (2013.01); *G01N 35/00029* (2013.01); *G01N 35/00732* (2013.01); *G01N 35/00871* (2013.01); *G16H 10/60* (2018.01); *G16H 30/40* (2018.01); *G16H 50/20* (2018.01); *G16H 80/00* (2018.01); *B01L 2300/021* (2013.01); *B01L 2300/12* (2013.01); *G01N 2035/00772* (2013.01); *G01N 2035/00831* (2013.01); *G01N 2035/00851* (2013.01); *G01N 2035/00881* (2013.01)

(58) Field of Classification Search
CPC .............. B01L 3/508; B01L 2300/021; B01L 2300/12; G01N 1/312; G01N 35/00029; G01N 35/00732; G01N 35/00871; G01N 2035/00772; G01N 2035/00831; G01N 2035/00851; G01N 2035/00881; G16H 10/60; G16H 30/40; G16H 50/20; G16H 80/00
See application file for complete search history.

(56) References Cited

U.S. PATENT DOCUMENTS

| | | |
|---|---|---|
| 5,817,032 A | 10/1998 | Williamson et al. |
| 6,246,785 B1 | 6/2001 | Molnar et al. |
| 7,156,814 B1 | 1/2007 | Williamson, IV et al. |
| 8,463,741 B2 * | 6/2013 | Ehlke ..................... G16H 30/00 707/608 |
| 2009/0226065 A1 | 9/2009 | Chen |
| 2010/0167334 A1 | 7/2010 | Williamson, IV |
| 2011/0125526 A1 | 5/2011 | Gustafson |
| 2012/0329140 A1 | 12/2012 | Iqbal et al. |
| 2014/0073004 A1 | 3/2014 | Williamson, IV et al. |
| 2014/0135236 A1 | 5/2014 | Musat |
| 2014/0273063 A1 | 9/2014 | Baust et al. |
| 2016/0085913 A1 | 3/2016 | Evans et al. |

FOREIGN PATENT DOCUMENTS

WO     2016013949 A2     1/2016

OTHER PUBLICATIONS

Neeraj Sharma et al., Segmentation and classification of medical images using texture-primitive features: Application of BAM-type artificial neural network, 33(3) J Med Phy 119-126 (Year: 2008).*
Ciaran Cunniffe, The Role of Aperio GENIE Image Analysis Tool in Modern Histopathology, The Pathology Company—Leica BioSystems (available at https://www.semanticscholar.org/paper/The-Role-of-Aperio-GENIE-Image-Analysis-Tool-in-Cunniffe/28bdc353c500d08b67eff9871d7f659c85321696) (Year: 2015).*
International Search Report, PCT Application No. PCT/US2018/017628, dated May 23, 2018.
Written Opinion of the International Searching Authority, PCT Application No. PCT/US2018/017628, dated May 23, 2018.
Themis Biopsy Chip™ advertising circular, Courtesy of "Carol Davila" Central Military Emergency University Hospital, Bucharest, Romania, Themis Biopsy Chip™ Version 1.7. Feb. 2016.

* cited by examiner

*Primary Examiner* — Sheetal R Paulson
*Assistant Examiner* — Jordan L Jackson
(74) *Attorney, Agent, or Firm* — FisherBroyles, LLP

(57) ABSTRACT

Tissue sample management systems include a central network, a medical professional system, and a pathology lab system for processing a tissue sample in a matrix having a sectionable code. At least the pathology lab system includes at least one imaging device, and the central network is configured to process images from the at least one imaging device to identify and record at least the sectionable code of the matrix. Methods for tissue sample processing include providing a matrix having a sectionable code and measurement marks, the matrix for receiving a tissue sample, and identifying the sectionable code from an image taken of the tissue sample in the matrix. Tissue sample-receiving matrices include a sectionable alphanumeric code or bar code, a tissue sample receptacle, and measurement marks formed along a sidewall thereof. The matrices include one or more proteins and one or more lipids.

9 Claims, 5 Drawing Sheets

SYSTEMS AND METHODS FOR TISSUE SAMPLE PROCESSING

CROSS-REFERENCE TO RELATED APPLICATIONS

This application claims the benefit under 35 U.S.C. § 119(e) of U.S. Provisional Patent Application Ser. No. 62/556,910, filed Sep. 11, 2017, and of U.S. Provisional Patent Application Ser. No. 62/457,078, filed Feb. 9, 2017, the disclosure of each of which is hereby incorporated herein in its entirety by this reference.

TECHNICAL FIELD

Embodiments of the application relate to systems and methods for tissue sample processing, such as for pathological procedures.

BACKGROUND

When a medical professional perceives a risk of cancer or other abnormality in an organ of a patient, the medical professional may take a tissue sample from the organ for analysis by a pathologist. In some known biopsy processes, the tissue sample is placed in a tissue sample cassette and the cassette is labeled, such as with a barcode or serial number, and associated with the patient. Depending on the specific procedure as well as on the type of tissue sample—the tissue sample can be placed on or in a tissue sample-receiving matrix in an attempt to maintain orientation and physical integrity of the tissue sample, and both the matrix and tissue sample are placed within the cassette. The cassette and tissue sample are transferred to a histopathology lab that is usually off-site from the location where the tissue sample was taken.

The histopathology lab receives the cassette and tissue sample and processes the tissue sample for microscopic evaluation. In some histopathology procedures, the tissue sample may be chemically fixed, dehydrated, embedded in paraffin wax material, and molded to form a paraffin wax block including the tissue sample. The paraffin wax block and tissue sample therein may be sliced into thin sections with a microtome. The thin sections may be positioned on glass slides for examination under a microscope by a pathologist. The pathologist may attempt to identify and locate abnormal tissue, such as cancerous cells, in the tissue sample. The results of the histopathological examination of the tissue sample may be communicated back to the medical professional and patient.

BRIEF SUMMARY

In some embodiments, tissue sample management systems include a central network, a medical professional system in communication with the central network, and a pathology lab system in communication with the central network. The central network includes at least one processor and a database. The medical professional system includes at least one first data input device, which is configured for inputting information about a tissue sample. The pathology lab system includes at least one imaging device and at least one second data input device, which may be configured for taking images of the tissue sample and a corresponding matrix including sectionable code. The central network is configured to receive data from the at least one first data input device and from the at least one second data input device, and to process the images taken by the at least one imaging device to identify and record at least the sectionable code of the matrix.

In some embodiments, methods for tissue sample processing include providing a matrix having a sectionable code and measurement marks, the matrix for receiving a tissue sample, taking a first image of the tissue sample in the matrix, transmitting the first image to a central network, identifying, from the first image, the sectionable code with a processor of the central network, digitally storing the sectionable code in a database of the central network, correlating the stored sectionable code with identification information of a patient from which the tissue sample was obtained, taking a second image of the tissue sample in the matrix having the sectionable code and measurement marks after at least some pathological processing, transmitting the second image to the central network, identifying, from the second image, the sectionable code with the processor, identifying, from the second image, the measurement marks with the processor, and correlating the second image with the identification information of the patient from which the tissue sample was obtained. The matrix is configured to exhibit a shrinkage rate substantially the same as a shrinkage rate of the tissue sample when subjected to a pathological process.

In some embodiments, tissue sample-receiving matrices include a sectionable alphanumeric code, at least one tissue sample receptacle, and measurement marks formed along at least one sidewall of the at least one tissue sample receptacle. The tissue sample-receiving matrix includes a material comprising one or more proteins and one or more lipids.

In some embodiments, tissue sample-receiving matrices include a sectionable machine-readable barcode, at least one tissue sample receptacle, and measurement marks formed along at least one sidewall of the at least one tissue sample receptacle. The tissue sample-receiving matrix also includes a material comprising one or more proteins and one or more lipids.

DETAILED DESCRIPTION

The following description provides specific details, such as material types, material thicknesses, and processing conditions in order to provide a thorough description of embodiments of this disclosure. However, a person of ordinary skill in the art will understand that the embodiments of this disclosure may be practiced without employing these specific details. Indeed, the embodiments of this disclosure may be practiced in conjunction with conventional techniques, systems, and materials employed in the industry.

In the following detailed description, reference is made to the accompanying drawings, which form a part hereof, and in which is shown, by way of illustration, specific embodiments in which the disclosure may be practiced. These embodiments are described in sufficient detail to enable a person of ordinary skill in the art to practice this disclosure. However, other embodiments may be utilized, and structural, material, procedural, and other changes may be made without departing from the scope of the disclosure. The illustrations presented herein are not meant to be actual views of any particular system, device, structure, or process, but are idealized representations that are employed to describe the embodiments of the disclosure. The drawings presented herein are not necessarily drawn to scale.

As used herein, any relational term, such as "upper," "left," "right," "bottom," etc., is used for clarity and convenience in understanding the disclosure and accompanying drawings and does not connote or depend on any specific preference, orientation, or order, except where the context clearly indicates otherwise.

As used herein, the term "substantially" in reference to a given parameter, property, or condition means and includes to a degree that one skilled in the art would understand that the given parameter, property, or condition is met with a small degree of variance, such as within acceptable manufacturing tolerances. For example, a parameter that is substantially met may be at least about 90% met, at least about 95% met, or even at least about 99% met.

Figure 1A:
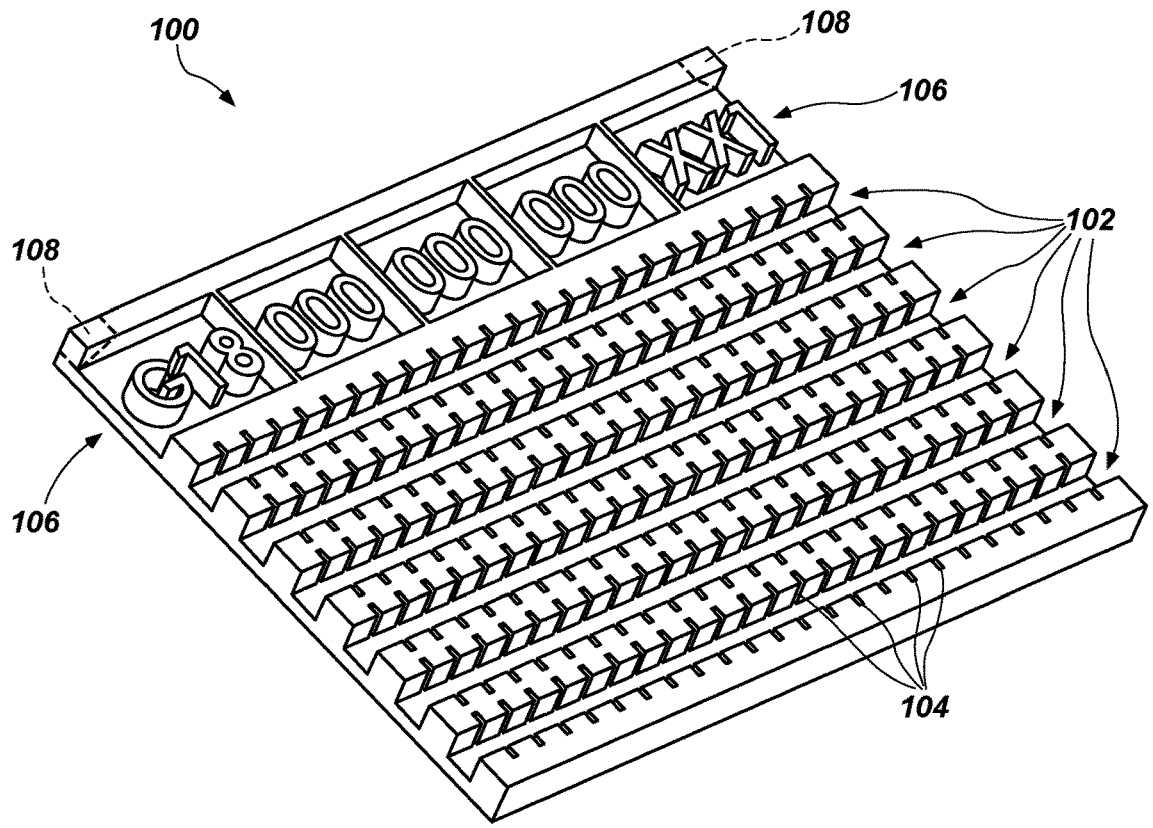
FIG. 1A shows a perspective view of a tissue sample receptacle according to an embodiment of this disclosure.
Figure 1B:
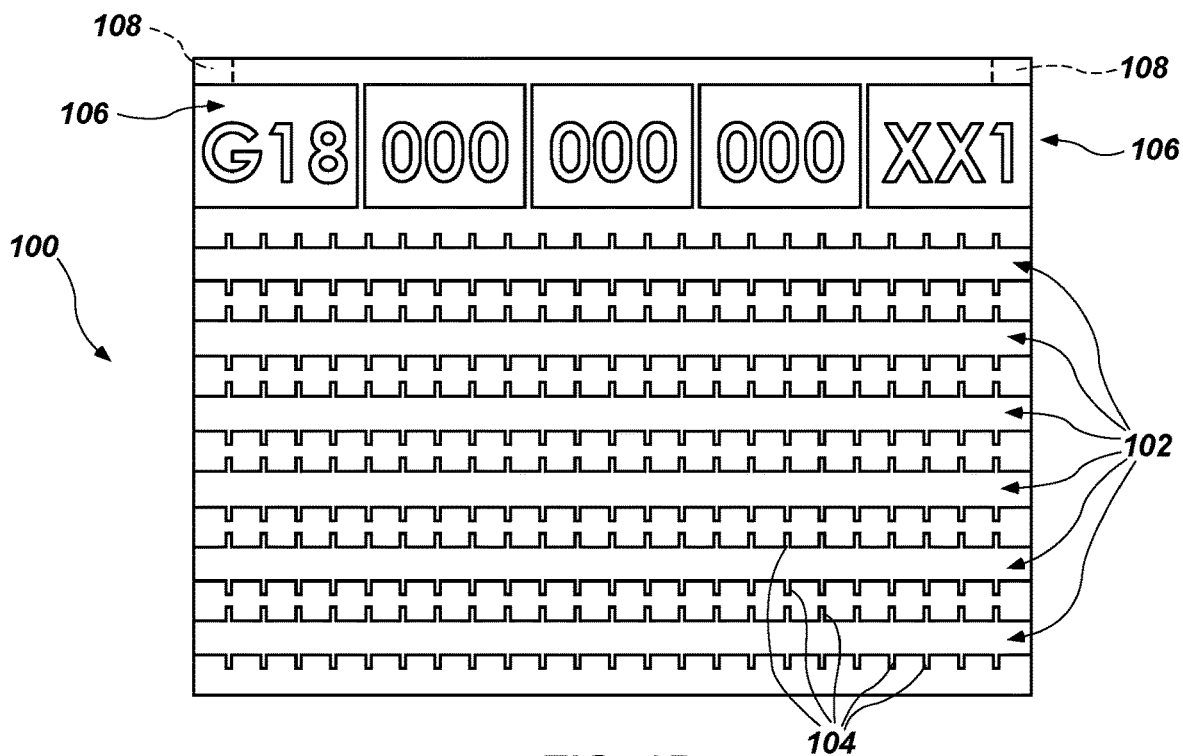
FIG. 1B shows a top view of the tissue sample-receiving matrix of FIG. 1A.

FIG. 1A shows a perspective view of a tissue sample-receiving matrix 100 according to an embodiment of this disclosure. FIG. 1B shows a top view of the tissue sample-receiving matrix 100 of FIG. 1A. The tissue sample-receiving matrix 100 is also referred to herein as a matrix 100. The matrix 100 may be formed of a material that includes one or more proteins and one or more lipids, each at varying concentrations. The presence, type, and concentrations of the one or more proteins and one or more lipids may enable the material of the matrix 100 to be tuned to the specific type of tissue to be pathologically processed with the matrix 100. Various types of tissue have different lipid contents. For example, breast and brain tissues have a relatively high lipid concentration, while prostate, kidney, and muscle tissues have relatively lower lipid concentrations. The different lipid concentrations of the different types of tissue result in different shrinkage rates during pathological tissue processing, since lipids and water are typically removed during pathological tissue processing. Tuning the matrix 100 to a particular tissue type may include selecting types and concentrations of the one or more proteins and of the one or more lipids to substantially match the shrinkage rate of the particular tissue type. Accordingly, the matrix 100 may be configured for shrinking during pathological tissue processing at substantially the same rate as a particular tissue sample to be processed with the matrix 100.

Example suitable materials for the matrix 100 are described in U.S. patent application Ser. No. 14/129,377, titled "MATRIX FOR RECEIVING A TISSUE SAMPLE AND USE THEREOF," filed Dec. 26, 2013, and issued as U.S. Pat. No. 9,851,349 on Dec. 26, 2017, the entire disclosure of which is incorporated herein by reference. By way of example and not limitation, and depending on the tissue type to be processed with the matrix 100, the material of the matrix 100 may include about 2% to about 14% w/v one or more proteins (including animal-based proteins, plant-based proteins, and/or synthetic proteins) and about 2.1% to about 20% w/v one or more lipids (including animal-based lipids, plant-based lipids, and/or synthetic lipids). The material of the matrix 100 may also include one or more of: about 2% to about 15% w/v glycerin; about 1% to about 10% antifoaming agent (e.g., agarose); an inorganic buffer in a concentration of from about 10 to about 600 mM; a gelling agent (e.g., a carbohydrate such as alginate, carrageenan, konjac gum, etc.); and water.

In some embodiments, the matrix 100 may be sized, shaped, and configured to maintain one or more tissue samples in an initial orientation throughout pathological processing. For example, as shown in FIGS. 1A and 1B, the matrix 100 may be configured for receiving needle core biopsy tissue samples by including a plurality of tissue sample receptacles 102 (also referred to as channels 102) sized and shaped for receiving the respective needle core biopsy tissue samples. Thus, the matrix 100 may be provided with channels 102 having different widths and/or lengths, such as to accommodate needle core biopsies taken using needles of different diameters and lengths. As shown in FIGS. 1A and 1B by way of example, the matrix 100 may include six channels 102. In additional embodiments, the matrix 100 may include another number of channels, such as two, three, four, five, eight, ten, or twelve, for example. A size of the matrix 100 may be altered to accommodate more or fewer channels 102.

Measurement marks 104 may be formed in the matrix 100 adjacent to and between the plurality of channels 102, such as along sidewalls of the matrix 100 defining the channels 102. The measurement marks 104 may be positioned at predetermined, known initial intervals, such as, for example, at initial intervals of 1 mm, 2 mm, 5 mm, 0.1 inch (0.254 cm), 0.2 inch (0.508 cm), 0.25 inch (0.635 cm), etc., along and adjacent to the plurality of channels 102. As used herein, the term "initial intervals" refer to the intervals as measured when the matrix 100 is formed and/or when the matrix 100 receives a tissue sample therein or thereon. The intervals between the measurement marks 104 may change (e.g., shrink) during pathological processing of the matrix 100 and corresponding tissue sample, such as due to water and/or lipid loss. As noted above, when the matrix 100 is properly tuned to the particular tissue sample being processed together with the matrix 100, the matrix 100 may exhibit a shrinkage rate that is substantially the same as the particular tissue sample. Thus, any portion of the tissue sample may have a position relative to the matrix 100 that is substantially maintained throughout pathological processing. An initial length, size, and position of a portion of the tissue sample (e.g., a cancerous portion), as originally present when the tissue sample was taken and from a patient and placed on the original matrix 100, may be ascertained after any shrinkage resulting from pathological processing. For example, the initial position of a portion of the tissue sample may be determined by counting the measurement marks 104 from an end of the processed tissue sample to determine the number of initial intervals and, therefore, original distance where the portion of interest was located on the tissue sample.

The measurement marks 104 may be defined by slits in the material of the matrix 100. The measurement marks 104 may extend partially (as shown in FIGS. 1A and 1B) or fully across portions of the matrix 100 adjacent to and between the plurality of channels 102. The measurement marks 104 may have a depth that is at least as great as the channels 102, such that the measurement marks 104 may be present in later-formed horizontal sections of the matrix 100 that also include a portion of a tissue sample within one or more of the channels 102. As shown in FIGS. 1A and 1B, the measurement marks 104 may be formed along both sides of each of the channels 102. However, in other embodiments, the measurement marks 104 may be formed only along one side of each of the channels 102.

The matrix 100 may also include a sectionable code 106 for unique and positive identification and digital registration of the matrix 100, the tissue sample received therein or thereon, and other corresponding data (e.g., patient information, medical professional information, procedural information, etc.) at various stages of processing. As used herein, the term "sectionable" refers to a feature that may be present in each section of a matrix including a tissue sample, such that the sectionable feature is present on each resulting slide including a tissue sample. The sectionable code 106 may be positioned proximate to and along a lateral side or end of the matrix 100. The sectionable code 106 may be any code that is machine-readable and/or human-readable. For example, as shown in FIGS. 1A and 1B, the sectionable code 106 may be or include a series of alphanumeric symbols. The sectionable code 106 may be provided as raised alphanumeric symbols (as shown in FIGS. 1A and 1B) or as alphanumeric depressions within a surrounding material of the matrix 100. Alternatively or additionally, the sectionable code 106 may be provided as portions of the matrix 100 that are distinguishable, such as by color or texture, from surrounding portions of the matrix 100. The sectionable code 106 may extend from a top surface of the matrix 100 to a depth at least as great as the channels 102, such that the sectionable code 106 may be present in later-formed horizontal sections of the matrix 100 that also include a portion of a tissue sample within one or more of the channels 102. Providing the sectionable code 106 in the matrix 100 itself may reduce or eliminate the conventional need to manually label the tissue cassette containing the tissue sample and matrix 100. In addition, the matrix 100 and tissue sample can be identified and tracked regardless of whether the same tissue cassette is used throughout the pathological process.

Although the sectionable code 106 is described above and shown in FIGS. 1A and 1B as alphanumeric characters, this disclosure is not so limited. Rather, the sectionable code 106 may be any human-readable and/or machine-readable representation of data that is configured and positioned to be present in horizontal sections made of the matrix that also include portions of a corresponding tissue sample. The sectionable code 106 may be compatible with and visible after (and during) histological processing, including after histological staining. The sectionable code 106 may be or include symbols that are alphanumeric, binary, colors, geometric patterns and shapes, lines, bars, rectangles, dots, hexagons, cylinders, prisms, cubes, etc. For example, the sectionable code 106 may be a barcode, as described below and shown in FIG. 5. In additional embodiments, the sectionable code 106 may be absent.

Referring again to FIGS. 1A and 1B, optionally, the matrix 100 may include at least one depth gauge 108 to facilitate determining a depth of a section taken from the matrix 100 and corresponding tissue sample. By way of example, the at least one depth gauge 108 may include a sloped surface extending at least through a depth of the plurality of channels 102, as shown in FIGS. 1A and 1B by dashed lines. For example, the sloped surface may have an angle of about 3 to 45 degrees relative to a bottom surface of the matrix 100. Thus, a shape and/or length of a portion of the matrix 100 adjacent to the at least one depth gauge 108 may change depending on a depth at which a section of the matrix 100 is taken. Identifying the lateral position of the at least one depth gauge 108 as it appears in a particular section may provide information as to the depth (e.g., a depth relative to other sections or an absolute depth) at which the section was taken. Although the at least one depth gauge 108 is illustrated in FIGS. 1A and 1B as being positioned in upper left and upper right corners of the matrix 100, the at least one depth gauge 108 may be positioned at one or more other locations in the matrix 100. In addition, more than two depth gauges 108 may be present, such as to identify depth with additional accuracy even if the matrix 100 is not positioned horizontally within a paraffin wax block.

In other embodiments, the at least one depth gauge 108 may be a series of features (e.g., depressions, blind holes, pillars) formed at different depths within the matrix 100. The presence or absence of a particular feature in the series of features in a section of the matrix 100 may provide information as to the depth at which the section was taken.

In some embodiments, the material of the matrix 100 may be stained to provide contrast with embedding and/or tissue sample materials, such as for clearer identification and distinction of the measurement marks 104, the sectionable code 106, and/or the at least one depth gauge 108.

By way of example and not limitation, the matrix 100, including the channels 102, measurement marks 104, sectionable code 106, and, if present, the at least one depth gauge 108, may be formed using a mold, a die cutter, a laser engraving device, or an end mill device. In some embodiments, a sheet of material for the matrix 100 may be formed, and the sheet of material may be cut using a laser engraving device or an end mill device with or without computer-controlling capabilities. Such example engraving techniques may be used to form the channels 102, the measurement marks 104, the sectionable code 106 (which may be unique to each matrix 100 formed), and/or the at least one depth gauge 108.

Figure 2:
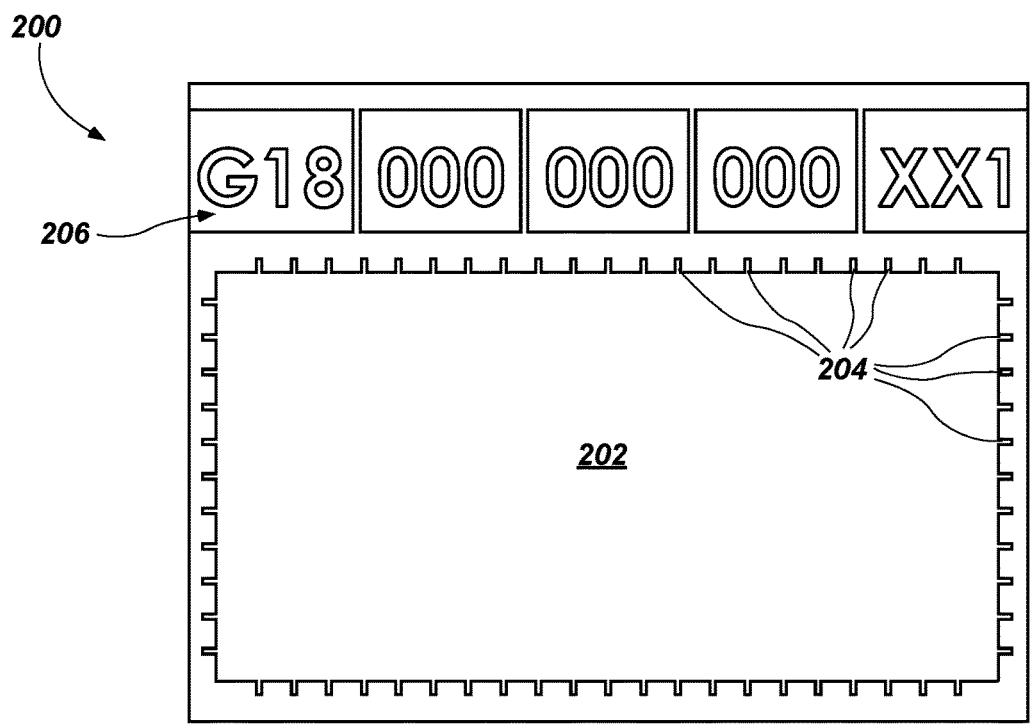
FIG. 2 shows a top view of a tissue sample-receiving matrix according to another embodiment of this disclosure.

FIG. 2 shows a top view of a tissue sample-receiving matrix 200 (also referred to herein as a matrix 200 for simplicity) according to another embodiment of this disclosure. The matrix 200 may be formed of a material that is tunable to (i.e., customizable to exhibit a substantially similar shrinkage rate as) different tissue types, as discussed above. The matrix 200 may be configured to receive a tissue sample that is not a needle core biopsy, such as an incisional biopsy, excisional biopsy, liquid specimens (e.g., urine sample or blood sample), or gelatinous specimens (e.g., gelatinized liquid specimens). Such tissue samples may not effectively fit within elongated channels. Accordingly, the matrix 200 may include at least one central tissue sample receptacle 202 (also referred to herein as a central receptacle 202), such as the central rectangular receptacle 202 shown in FIG. 2. In some embodiments, the matrix may include more than one central receptacle 202, such as, but not limited to, four central receptacles 202 (e.g., one in each quadrant of the matrix 200).

The central receptacle 202 may be at least partially surrounded by one or more protrusions in the matrix 200, which may include measurement marks 204, as described above. The measurement marks 204 may be present along one, two, three, or all four lateral sides of the central receptacle 202. The matrix 200 may also include a sectionable code 206, as described above.

Thus, the matrices 100, 200 according to this disclosure may be configured for receiving and being processed together with different tissue and biopsy types, shapes, and sizes. A variety of matrices 100, 200 having different material properties (e.g., protein, lipid, and/or carbohydrate concentrations) for substantially matching shrinkage rates of various tissue types (e.g., prostate, breast, liver, brain, muscle, kidney, etc.) may be provided. In addition, a variety of matrices 100, 200 may be provided for tissue samples taken using different procedures, such as needle core biopsies, incisional biopsies, and excisional biopsies of different shapes and sizes. The original orientation and position of the tissue samples or any portion thereof may be preserved, determined, recorded, and registered by using the measurement marks 104, 204 or other identifiers on or in the matrices 100, 200. Each instance of the matrices 100, 200 may be provided with a unique sectionable code for identification and correlation of the matrices 100, 200 and corresponding tissue samples at any stage of pathological processing. Optionally, in some embodiments, a tracking device, such as a radio frequency identification ("RFID") chip, may be provided within the matrices 100, 200 or attached to the matrices 100, 200, for additional tracking capabilities of the matrices 100, 200 during processing.

Figure 3:
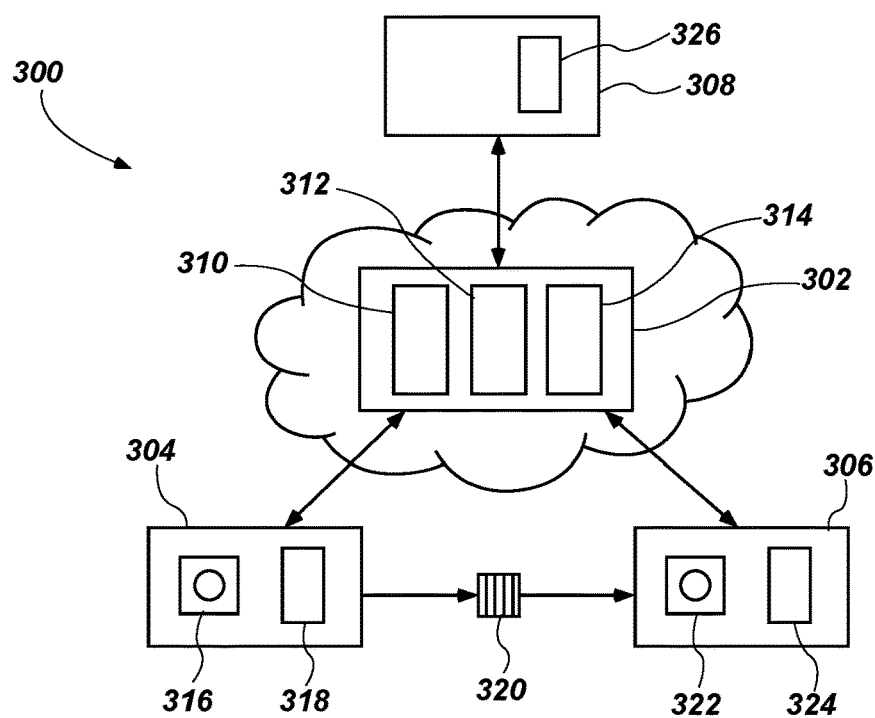
FIG. 3 illustrates a block diagram of a tissue sample management system according to an embodiment of this disclosure.

FIG. 3 illustrates a block diagram of a tissue sample management system 300 according to an embodiment of this disclosure. The tissue sample management system 300 may include features that are similar to the system disclosed in U.S. patent application Ser. No. 14/771,427, titled "System, Method, and Apparatus for Documenting and Managing Biopsy Specimens and Patient-Specific Information On-Site," filed Aug. 28, 2015, published as U.S. Patent Application Publication No. 2016/0085913 on Mar. 24, 2016 (hereinafter "the '913 Publication"), the entire disclosure of which is incorporated herein by reference. The tissue sample management system 300 may include a central network 302, a medical professional system 304 in communication with the central network 302, and a pathology lab system 306 in communication with the central network 302. Optionally, an artificial intelligence (AI) system 308 (or expert system) may also be in communication with the central network 302. The communications between the central network 302 and the medical professional system 304, the pathology lab system 306, and the AI system 308 may be accomplished by one or more of a wireless link (e.g., WiFi, WiMAX, cellular, PCS, 3G, 4G, LTE, etc.) and a wired link (e.g., Ethernet, cable, fiber optic, etc.).

The central network 302 may include a server 310, a central processor 312, and a database 314. The central network 302 may be a so-called "cloud" network that is remote from the medical professional system 304, pathology lab system 306, and AI system 308. Alternatively, the central network 302 may be physically located proximate to one or both of the medical professional system 304 or the pathology lab system 306, such as at a hospital or medical complex. The server 310 may interact with clients including the medical professional system 304, pathology lab system 306, and AI system 308. The database 314 may be used to register, store, correlate, and recall data from the medical professional system 304, the pathology lab system 306, and the AI system 308, such as patient data (e.g., patient identification, patient medical records, allergies, etc.), tissue sample data (e.g., type of tissue, size of the tissue sample, type of biopsy taken, location on organ or body of patient from which the tissue sample was taken, orientation of the tissue sample, location of potentially abnormal cells on tissue sample, etc.), matrix data (e.g., type of matrix, composition of matrix, sectionable code in matrix, initial intervals of measurement marks on matrix, etc.), medical professional data (e.g., identification of medical professional, contact information of medical professional, etc.), and pathology procedure data (e.g., time of procedural steps, type and concentration of chemicals used in procedure, pathologist identification, pathology lab identification, etc.). The central network 302 may be linked to the medical professional system 304 and to the pathology lab system 306 in such a manner to both receive information therefrom and to provide information thereto.

The medical professional system 304 may include at least one first imaging device 316 (e.g., digital camera, scanner, cellular telephone camera, webcam, tablet camera, etc.) for taking images of tissue samples and corresponding matrices obtained from a patient by a medical professional. The images may be digitally sent from the medical professional system 304 to the central network 302 for registration, storage, and processing thereof. In some embodiments, the at least one first imaging device 316 may be a specialized camera configured for taking images of a tissue sample and matrix, such as within a tissue cassette. By way of example and not limitation, the at least one first imaging device 316 may be configured as shown and described in the '913 Publication incorporated by reference above.

The medical professional system 304 may also include at least one first data input device 318. The at least one first data input device 318 may include one or more of a mobile device, a desktop computer, a tablet, or a laptop computer, for example. The at least one first data input device 318 may be provided for receiving input from a medical professional, such as an identification of a patient, an identification of an organ or body part from which a tissue sample is taken, an identification of a type of biopsy procedure to be performed (e.g., needle core biopsy, incisional biopsy, excisional biopsy), notes regarding the reasons for taking the biopsy, etc. The at least one first data input device 318 may be programmed to guide the medical professional through the data input process, such as by providing options for selection (in the form of, for example, illustrations of organs, lists, menus, etc.), information for verification, and/or fields for textual data entry. The sectionable code of a particular matrix that has received a tissue sample may be input or verified by the medical professional. The at least one first data input device 318 may be in communication with the at least one first imaging device 316 for receiving images therefrom. The at least one first data input device 318 may be programmed to display images from the at least one first imaging device 316 for review, verification, and/or notation by the medical professional. Data may be transmitted from the at least one first data input device 318 to the central network 302.

The at least one first data input device 318 may also receive data from a guided biopsy system, such as a computerized tomography (CT) biopsy system, a magnetic resonance imaging (Mill) biopsy system, an X-ray biopsy system, or an ultrasound biopsy system. For example, a medical professional may use such a guided biopsy system to visualize the procedure while obtaining a tissue sample from an organ of a patient. The guided biopsy system may transmit images or video to the at least one first data input device 318 for recordation and correlation to the particular tissue samples obtained and a corresponding matrix. Such data from the guided biopsy system may be recalled at a later time to identify a particular, two-dimensional (2D) or three-dimensional (3D) location and orientation on or in an organ of a patient from which a tissue sample of interest was taken. The location and orientation of a tissue sample of interest may be compared to a position of abnormal cells as determined by a pathologist or by the AI system 308 after the tissue sample is pathologically processed. Identification of an original position and orientation of the abnormal cells relative to an original tissue sample may be facilitated using the measurement marks in the matrix, even when the tissue sample experiences a significant shrinkage, as described above. A digital 3D model of the organ from which the tissue sample was taken may be generated and the tissue sample may be superimposed with the digital 3D model to visualize the original position and orientation from which the tissue sample was obtained. In addition, a position of any abnormal (e.g., cancerous) portion of the tissue sample may be identified on the digital 3D model.

After a tissue sample is placed in or on a matrix and any imaging and data entry are completed by a medical professional, and the matrix and tissue sample are placed in a tissue cassette, the tissue cassette 320 may be transferred from the medical professional system 304 to the pathology lab system 306. The pathology lab system 306 may include at least one second imaging device 322 and at least one second data input device 324. The at least one second imaging device 322 may be used to take images of the tissue sample and corresponding matrix (including the measurement marks and sectionable code therein) at any step of a pathology process, including but not limited to reception of tissue cassette 320 from the medical professional system 304, gross examination, fixation, dehydration, clarification, infiltration, embedding, sectioning, and slide preparation and review. In some embodiments, the at least one second imaging device 322 may be a specialized camera configured for taking images of a tissue sample and matrix, such as within a tissue cassette. By way of example and not limitation, the at least one second imaging device 322 may be configured as shown and described in the '913 Publication incorporated by reference above.

The at least one second data input device 324 may be used by a pathologist or lab technician to input and/or verify data regarding, for example, the tissue sample, the matrix, the pathology procedure to which the tissue sample and matrix are subjected, the identification of any abnormal tissue, etc. The at least one second data input device 324 may receive images from the at least one second imaging device 322 for review and/or notation by a pathologist or lab technician or for processing by the AI system 308. Data and images may be transmitted from the pathology lab system 306 to the central network 302 and, optionally, to the AI system 308. Additionally or alternatively, data and images may be transmitted from the pathology lab system 306 to the medical professional system 304 (e.g., directly or indirectly through the central network 302) for review by a medical professional.

The AI system 308 may be a standalone system in communication with the central network 302, as depicted in FIG. 3. Alternatively, the AI system 308 may be an integral part of the central network 302, of the medical professional system 304, or of the pathology lab system 306, for example. The AI system 308 may include an AI processor 326 programmed to process images of tissue samples and matrices (e.g., the matrices 100, 200 described above with reference to FIGS. 1A, 1B, and 2), such as to identify and locate cellular material of interest in the tissue samples (e.g., for identifying cancerous tissues, to identify benign tissues, for primary cancer screening, for providing a cancer diagnosis, for grading cancerous lesions, etc.), to interpret measurement marks, to identify depth gauges, to distinguish between tissue samples and adjacent portions of the matrices, to measure features of the tissue samples (e.g., to identify a length, width, and depth of the tissue samples or an identified portion thereof), to determine a percent involvement (i.e., a percentage of a total tissue area) of identified abnormal cells (whether identified by the AI system 308 or by a pathologist, for example), and/or to identify sectionable code in the matrices. The AI processor 326 may be programmed to correlate the identified abnormal cells in the tissue samples with particular measurement marks in the matrix to determine an initial (e.g., prior to pathological processing) location of the abnormal cells on the tissue sample. The AI processor 326 may also be programmed to correlate a particular tissue sample and images thereof with a particular sectionable code in the corresponding matrix, for digitally registering the matrix and tissue sample and correlating the matrix and tissue sample to the patient from which the tissue sample was obtained. Additionally, the AI system 308 may be configured to facilitate a diagnostic process, such as by analyzing a digital image (e.g., a whole slide image) and identifying and locating abnormal cells of interest (e.g., cancerous cells) and/or normal cells that are not of interest in diagnosis. As an example, the AI system 308 may be configured and programmed using tools that are known in the art, such as AI tools available from Google LLC of Mountain View, Calif., and available online at https://ai.google/. Machine learning may be utilized to develop the AI system 308 for recognizing abnormal cells, distinguishing tissue samples from surrounding matrices, and/or for performing other tasks, as described herein. In some embodiments, the computing, storage, and networking capabilities may be provided locally and/or through a remote service, such as cloud computing through third party vendors.

In some embodiments, the AI system 308 may be used at one or more stages of a pathological process. By way of example and not limitation, the AI system 308 may be configured to identify sectionable code in the matrix at any stage of the pathological processing in which the sectionable code is visible, such as during a gross examination, after partial processing, and/or after full processing (e.g., a prepared slide). The AI system 308 may be configured to take gross measurements from an image of the tissue sample and matrix, such as by distinguishing the tissue sample from surrounding portions of the matrix and determining the measurements (e.g., length, width, surface area, position, etc.). The AI system 308 may be configured to receive information from a pathologist relating to a digital image of a prepared slide including a tissue sample and surrounding matrix material, such as an identified location of abnormal cells, and process that information further. For example, a pathologist may encircle abnormal cells on a digital image using the at least one first data input device 318 (e.g., a touchscreen) of the medical professional system 304, and the AI system 308 may determine a size, location, and percent involvement of the abnormal cells. Alternatively or additionally, the AI system 308 may itself identify abnormal cells from a digital image, and then may determine the size, location, and percent involvement of the abnormal cells. The AI system 308 may also be configured to correlate the location of the abnormal cells in the matrix to an original location of the abnormal cells in an organ of a patient from which the tissue sample was received.

Information may be transmitted to and from any of the central network 302, medical professional system 304, pathology lab system 306, and AI system 308 automatically or on demand (e.g., as demanded by a medical professional, pathologist, or lab technician). Accordingly, the tissue sample management system 300 may facilitate communication, registration, and evaluation of information relating to a tissue sample and a corresponding matrix. The sectionable code of a matrix, as described above with reference to FIGS. 1A, 1B, and 2, may facilitate the registration, evaluation, and correlation of data relating to a particular tissue sample. The measurement marks of a matrix, as described above with reference to FIGS. 1A, 1B, and 2, may facilitate an accurate identification of an original location, size, and shape of abnormal cells within a particular tissue sample.

Figure 4:
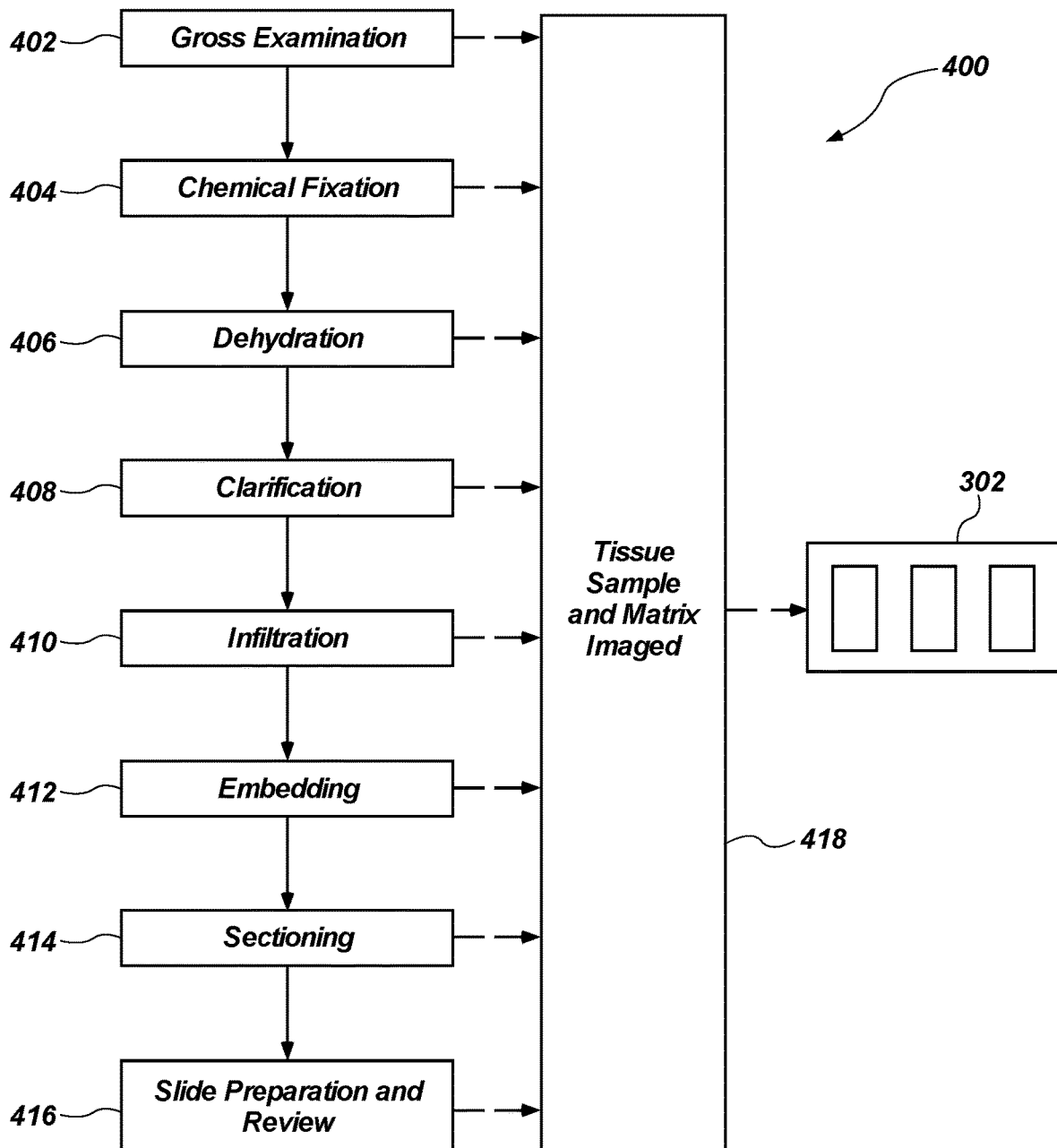
FIG. 4 illustrates a flow chart of a method of handling a tissue sample in a pathological process according to an embodiment of this disclosure.

FIG. 4 illustrates a flow chart of a method 400 of handling a tissue sample in a pathological process according to an embodiment of this disclosure. When a tissue sample is positioned within a corresponding matrix and/or received at a pathological lab, gross examination 402 may be performed by examining the tissue sample prior to further processing and modification. The gross examination 402 may be performed by direct observation of the tissue sample, or the gross examination 402 may be performed by reviewing an image taken (e.g., by a medical professional, by a lab technician, or by a pathologist) of the tissue sample. The tissue sample and corresponding matrix may be chemically fixed 404. Chemical fixation 404 may be accomplished by positioning the tissue sample and corresponding matrix within a fixative fluid, such as formalin, to physically fix major biochemical constituents of the tissue sample and matrix in place.

The tissue sample and matrix may be dehydrated 406 by exposure to ethanol solutions of increasing concentrations, up to 100% ethanol. The dehydration 406 process may remove substantially all water from the tissue sample and from the matrix. Additional components of the tissue sample and matrix may also be removed during dehydration 406, such as water soluble proteins and some lipids. Thus, the tissue sample and matrix may experience some shrinking.

The tissue sample and matrix may be clarified 408 by exposure to a clearing agent, such as xylene, to remove the ethanol and to replace the ethanol with the clearing agent. The clearing agent may be miscible with wax, such as paraffin wax. The clearing agent may also remove lipids from the tissue sample and matrix, resulting in additional shrinking.

Next, infiltration 410 may be accomplished by exposing the tissue sample and matrix to molten wax, such as paraffin wax. The wax may replace the clearing agent within the tissue sample and matrix, which may result in additional shrinking.

After infiltration 410, the infiltrated tissue sample and matrix may be positioned within a mold for embedding 412. In the embedding 412 process, additional molten wax (e.g., paraffin wax) may be added to the mold to create a wax block containing the infiltrated tissue sample and matrix. The wax may be cooled and hardened.

The wax block, including the embedded tissue sample and matrix therein, may be sectioned 414, such as by a microtome. The sectioning 414 may create thin sections of wax, tissue sample, and matrix. The measurement marks and sectionable code of the embedded matrix may be visible in each section containing portions of the embedded tissue sample. Accordingly, each section may be visually identified as belonging to a particular matrix and corresponding tissue sample. The depth gauge, if present, can provide information of the depth within the paraffin block form where individual sections originate.

Slides preparation and review 416 may include positioning the sections on respective slides for review under a microscope (or for imaging under a microscope for digital review). Optionally, the sections may be stained with a histology stain, such as to increase contrast of the tissue and/or to highlight specific tissue features of interest. The histology stain may be selected by a pathologist depending on the type of tissue or cellular material to be highlighted. A pathologist may review the sections or images thereof to identify abnormal (e.g., cancerous) cellular material, if any. Alternatively or additionally, images of the slides may be processed and reviewed by an AI system 308, as described above with reference to FIG. 3.

At any of the pathology process acts described above, the tissue sample and matrix may be imaged 418. The resulting image(s) may be transmitted to the central network 302 for identification, verification, registration, digital storage, association with the patient from which the tissue sample was taken, etc. Such processing by the central network 302 (and/or by the AI system 308, see FIG. 3) may be facilitated by the presence of the sectionable code, one or more tissue sample receptacles, measurement marks in the matrix, and/or depth gauges in the matrix, which may be discernible at any of the pathology process acts described above.

Figure 5:
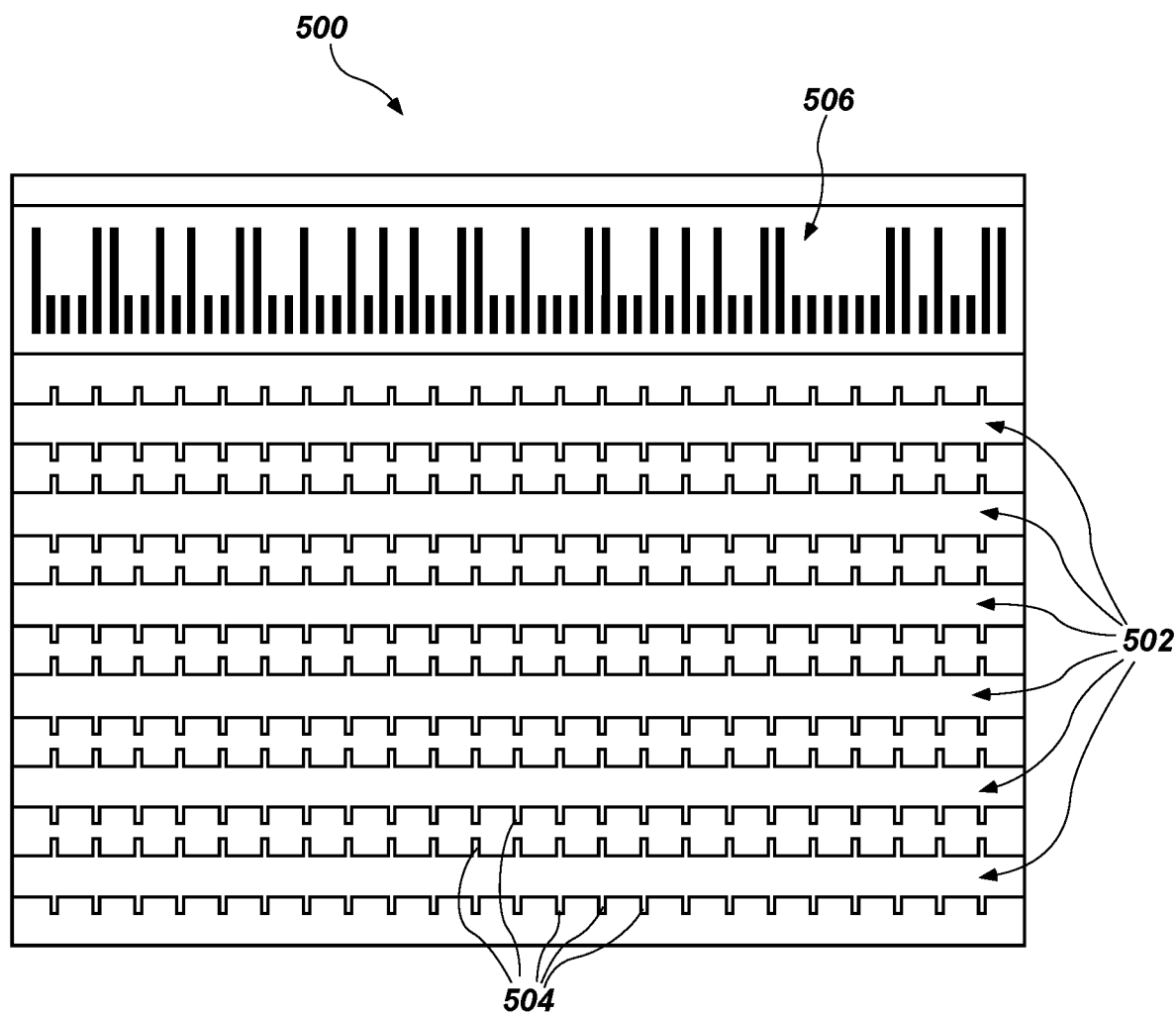
FIG. 5 shows a top view of a tissue sample-receiving matrix according to another embodiment of this disclosure.

Referring to FIG. 5, a top view of another embodiment of a tissue sample-receiving matrix 500 (also referred to herein as a matrix 500) is shown. The matrix 500 may be similar to the matrix 100 described above and shown in FIGS. 1A and 1B. Thus, the matrix 500 may include one or more tissue sample receptacles 502 (e.g., channels), measurement marks 504 along one or more sidewalls of the tissue sample receptacles 502, and a sectionable code 506. However, the sectionable code 506 of the matrix 500 may be implemented as a barcode, including bars of different lengths and/or widths. The sectionable code 506 may be machine-readable. The sectionable code 506 may include raised portions of the matrix 500, depressions in the matrix 500, and/or stained portions of the matrix 500. In further embodiments, both a barcode and an alphanumeric (or other human-readable or machine-readable) sectionable code may be included.

Figure 6:
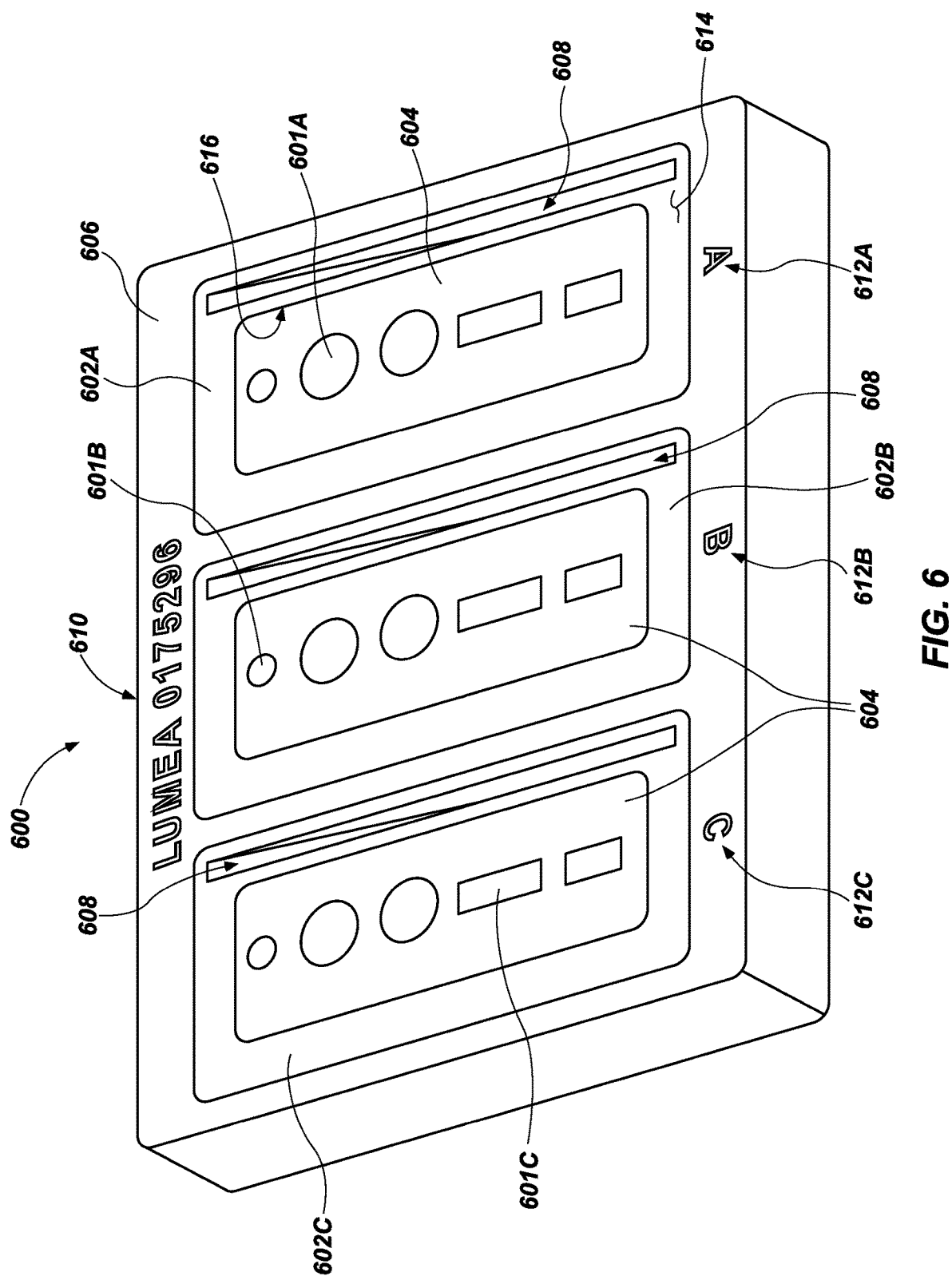
FIG. 6 shows a perspective view of a tissue sample-receiving matrix according to another embodiment of this disclosure.

Referring to FIG. 6, another embodiment of a tissue sample-receiving matrix 600 (also referred to herein as a matrix 600) is illustrated. The matrix 600 may be formed of a material that is tunable to (i.e., customizable to exhibit a substantially similar shrinkage rate as) different tissue types, as discussed above. The matrix 600 may be configured to receive at least one tissue sample 601 (including, for example, a first tissue sample 601A, a second tissue sample 601B, and a third tissue sample 601C) that is a needle core biopsy, incisional biopsy, excisional biopsy, liquid specimens (e.g., urine sample or blood sample), or gelatinous specimens (e.g., gelatinized liquid specimens). The at least one tissue sample 601 to be received by the matrix 600 may be unprocessed, partially processed, or fully processed. For example, the at least one tissue sample 601 may initially be a fresh tissue sample 601 taken directly from a patient, a partially processed tissue sample 601 (e.g., chemically fixed, dehydrated, clarified, and infiltrated, but not yet embedded or sectioned), or a fully processed tissue sample 601 (e.g., a portion of an embedded and sectioned tissue sample 601).

The matrix 600 may be configured to receive and maintain different tissue samples 601A, 601B, and 601C from a single patient or from respective different patients. For example, the matrix 600 may include a first carrier 602A, a second carrier 602B, and a third carrier 602C (collectively referred to as the carriers 602) for respectively receiving the different tissue samples 601A, 601B, and 601C. Each of the carriers 602 may include an outer, generally rectangular sidewall. A depth gauge 608 (e.g., a sloped surface) may be formed in or on the sidewall of each of the carriers 602. In some embodiments, the carriers 602 may each be distinguishable from each other, such as by using one or more colors (e.g., dyes), patterns, sectionable code, or other distinguishing features. The carriers 602 may be or include a tunable matrix material, as described above. In some embodiments, the carriers 602 may include a sectionable code, as described above. In some embodiments, the carriers 602 may include one or more sectionable measurement marks, as described above. The carriers 602 may be at least partially filled with a filler matrix material 604, in which the at least one tissue sample 601 may be embedded. The carriers 602 may be positioned within a support member 606, which may also be or include a tunable matrix material, as described above.

The support member 606 may include a sectionable code 610 for uniquely identifying the support member 606 and the matrix 600. In some embodiments, the support member 606 may also include sectionable carrier identifiers 612A, 612B, 612C (collectively referred to as sectionable carrier identifiers 612), which may be respectively positioned adjacent to the first carrier 602A, second carrier 602B, and third carrier 602C. Accordingly, a section taken from the entire matrix 600 may include the sectionable code 610 and the sectionable carrier identifiers 612 for uniquely identifying the each of the carriers 602 and the matrix 600.

In operation, by way of example, the matrix 600 and carriers 602 may be used as follows. The carriers 602 may initially have an adhesive film or substance positioned over an outer surface 614 thereof to cover an internal receptacle 616 thereof. The first tissue sample 601A may be taken (e.g., from a patient, from a partially or fully processed block including tissue, from a fully processed section of a block, etc.) and adhered to the adhesive film or substance over the first carrier 602A. The filler matrix material 604 may be positioned within the internal receptacle 616 over the first tissue sample 601A and allowed to harden. For example, the filler matrix material 604 may initially be in a liquid form when introduced into the internal receptacle 616, and then may be hardened by cooling, by curing over time, or by exposure to a catalyst. Optionally, a tracking device, such as an RFID chip, may be embedded within or attached to the filler matrix material 604, such as on a side thereof opposite the first tissue sample 601A.

Similarly, the second tissue sample 601B may be taken and adhered to the adhesive film or substance over the second carrier 602B, and the filler matrix material 604 may be positioned and hardened within the internal receptacle 616 of the second carrier 602B and over the second tissue sample 601B. Optionally, an RFID chip may be embedded within or attached to the filler matrix material 604 within the second carrier 602B. The third tissue sample 601C may be taken and adhered to the adhesive film or substance over the third carrier 602C, and the filler matrix material 604 may be positioned and hardened within the internal receptacle 616 of the third carrier 602C and over the third tissue sample 601C. Optionally, an RFID chip may be embedded within or attached to the filler matrix material 604 within the third carrier 602C. The tissue samples 601 may originate from a single patient or from multiple respective patients.

The carriers 602 prepared in this manner, including the tissue samples 601 and filler matrix material 604, may be positioned within a single support member 606 for additional processing, such as by performing one or more of the acts described above with reference to FIG. 4.

The matrix 600 may enable so-called "multiplexing" (i.e., simultaneous processing) of multiple tissue samples 601, including those from a single patient or from multiple different patients, while maintaining unambiguous identification of the tissue samples 601 using, for example, the sectionable code, RFID chip, and/or other identifying features (e.g., color, pattern, etc.). Multiplexing may result in significant cost savings, such as by reducing required labor, materials (e.g., dyes, chemicals, etc.), and processing time. In addition, the distinguishing features of the carriers 602 (e.g., colors, sectionable codes, etc.) and/or the sectionable carrier identifiers 612 may be recorded, associated with patient information, and/or registered, as described above either manually or using an AI system. Additionally, the sectionable code 610, sectionable carrier identifiers 612, and depth gauges 608 may be perceptible in any sectioned slide formed from the matrix 600. Thus, any section of the matrix 600 and tissue sample 601 may be uniquely identified, even if viewed separately from other sections made from the same matrix 600.

The matrices described in this disclosure may provide a standard platform for tissue handling, processing, imaging, and evaluation. Such a standard platform may improve consistency of tissue sample handling between different laboratories, reducing variability in tissue sample image production. In addition, tissue sample orientation within the matrices may be maintained more easily. Moreover, the configuration of the matrices disclosed herein may enable image processing of only a portion of the images of matrices and tissue samples, by providing distinguishing features in the matrices that may be used to separate portions of the images. Each of these potential improvements may facilitate (e.g., speed) the development and commercialization of AI processing and evaluation of tissue samples. The matrices may also facilitate evaluation and annotation of tissue samples by pathologists, such as for identifying abnormal cells in specific samples and/or for providing feedback data to the AI systems for improvement of the AI systems. Laboratory information systems (LIS) may be provided to include whole slide image annotation capabilities specifically for the development of AI systems and capabilities.

The embodiments of the disclosure described above and illustrated in the accompanying drawing figures do not limit the scope of the invention, since these embodiments are merely examples of embodiments of the disclosure. The invention is encompassed by the appended claims and their legal equivalents. Any equivalent embodiments lie within the scope of this disclosure. Indeed, various modifications of this disclosure, in addition to those shown and described herein, such as other combinations and modifications of the elements described, will become apparent to those of ordinary skill in the art from the description. Such embodiments, combinations, and modifications also fall within the scope of the appended claims and their legal equivalents.

What is claimed is:

1. A tissue sample management system comprising:
   a central network including at least a central processor and a database;
   a medical professional system in communication with the central network, the medical professional system including at least one first data input device, the at least one first data input device configured for inputting information about a tissue sample received in a matrix that includes sectionable code, wherein the sectionable code comprises a portion of the matrix that is configured to be embedded with the tissue sample after tissue processing, wherein the sectionable code further comprises a representation of data that is configured to be present in each section made of the matrix that also includes portions of the tissue sample; and
   a pathology lab system in communication with the central network, the pathology lab system including at least one imaging device and at least one second data input device, the at least one imaging device configured for taking images of at least one section of the tissue sample and the corresponding matrix including the sectionable code;

wherein the central network is configured to receive data from the at least one first data input device and from the at least one second data input device and to automatically process the images taken by the at least one imaging device to identify and record at least the sectionable code of the matrix.

2. The system of claim 1, further comprising a machine learning system in communication with the central network, the machine learning system configured to further process the images taken by the at least one imaging device to identify at least the sectionable code.

3. The system of claim 2, wherein the machine learning system is further configured to identify, from the images taken by the at least one imaging device, measurement marks formed in the matrix.

4. The system of claim 2, wherein the machine learning system is further configured to identify, from the images taken by the at least one imaging device, a location of cellular material of interest in the tissue sample.

5. The system of claim 2, wherein the machine learning system is further configured to identify, from the images taken by the at least one imaging device, gross measurements of the tissue sample.

6. The system of claim 2, wherein the machine learning system is further configured to distinguish the tissue sample from at least surrounding portions of the matrix.

7. The system of claim 2, wherein the machine learning system is further configured to correlate an identified portion of the tissue sample with an original location of the identified portion of the tissue sample on an organ of a patient from which the tissue sample was received.

8. The system of claim 2, wherein the machine learning system is further configured to determine an estimated value of the percent involvement of abnormal cellular material in the tissue sample.

9. The system of claim 1, wherein the medical professional system further comprises at least one additional imaging device configured for taking images of the tissue sample and the corresponding matrix including the sectionable code.

* * * * *